United States Patent [19]

Sanders et al.

[11] Patent Number: 5,151,470

[45] Date of Patent: Sep. 29, 1992

[54] AMINOCROTONATES AS CURING AGENTS FOR EPOXY RESINS

[75] Inventors: Joseph Sanders, Leverkusen, Fed. Rep. of Germany; Robson Mafoti, Pittsburgh, Pa.; Peter H. Markusch, McMurray, Pa.

[73] Assignee: Miles Inc., Pittsburgh, Pa.

[21] Appl. No.: 819,029

[22] Filed: Jan. 10, 1992

[51] Int. Cl.⁵ .............................................. C08G 59/52
[52] U.S. Cl. .................................... 525/407; 525/531; 528/111; 528/341; 528/361; 528/407
[58] Field of Search ............... 528/111, 341, 361, 407; 525/407, 531

[56] References Cited

U.S. PATENT DOCUMENTS

| | | | |
|---|---|---|---|
| 3,666,726 | 5/1972 | Grogler et al. | 260/77.5 CH |
| 3,691,112 | 9/1972 | Grogler et al. | 260/2.5 AM |
| 3,993,708 | 11/1976 | Brinkmann et al. | 260/830 P |
| 4,291,146 | 9/1981 | Haug | 528/119 |
| 4,360,655 | 11/1982 | Haug | 528/120 |
| 4,424,336 | 1/1984 | Haug | 528/117 |
| 5,021,537 | 6/1991 | Stark et al. | 528/106 |

FOREIGN PATENT DOCUMENTS

| | | |
|---|---|---|
| 363000 | 4/1990 | European Pat. Off. . |
| 1252606 | 10/1967 | Fed. Rep. of Germany . |
| 1411485 | 10/1975 | United Kingdom . |

*Primary Examiner*—John C. Bleutge
*Assistant Examiner*—Frederick Krass
*Attorney, Agent, or Firm*—Joseph C. Gil

[57] ABSTRACT

Specified aminocrotonates are described for use as hardeners for expoxide resins.

4 Claims, No Drawings

AMINOCROTONATES AS CURING AGENTS FOR EPOXY RESINS

BACKGROUND OF THE INVENTION

The present invention relates to the use of certain aminocrotonates as hardeners for epoxide resins.

Synthetic resins based on epoxide resins are distinguished by numerous positive properties, e.g. good adherence to organic and inorganic substrates, good solvent resistance and high chemical resistance. Due to their chemical structure, however, epoxide resins which have been hardened with amines are often brittle, with glass transition ranges above 20° C. This applies particularly to those epoxide resins which are based on 2,2-bis(4-hydroxyphenol)propane (bisphenol A) and epichlorohydrin. These synthetic resins therefore fail to meet the practical requirements in all fields of application for which a certain degree of flexibility is required. This applies particularly to the building industry, where permanent bridging of shrinkage cracks, e.g. in concrete, is required.

Internal increase in flexibility can be achieved to a certain extent by a reduction in the crosslink density while an external increase in flexibility may be achieved by the addition of plasticizer. External flexibilizing agents such as tar, phthalic acid esters, high boiling alcohols or vinyl polymers are not reactive and do not become incorporated in the polymer network.

An internal increase in flexibility by reduction of the crosslink density may be achieved by reducing the functionality of the hardener. The long chain, low functional amino amides based on dimerized fatty acids which have been widely and successfully used for a long time for this purpose are, however, not suitable in all fields.

Good and permanent increase in flexibility of the epoxide resins may be obtained by a combination with polyurethanes. Thus, for example, elasticized synthetic resins of epoxide resins, polyfunctional carbamic acid aryl esters and polyamines have been described in German Offenlegungsschrift 1,252,606. Synthetic resins prepared by these means have, however, two significant disadvantages. First, the use of a three component system is not always simple. Secondly, phenols or substituted phenols are released in the course of hardening of such synthetic resins since they are not chemically bound and in the long term they migrate from the synthetic resins, with the result that the properties of the product suffer.

German Auslegeschrift 2,418,041 describes a process for the preparation of elasticized molded parts and sheet products, in which certain epoxide compounds are reacted with amine compounds which have been obtained by the hydrolysis of certain prepolymeric ketimines or enamines. Chemically resistant, firmly adhering products with improved properties may be prepared by this process. The process described, however, is relatively complicated and therefore expensive. Further, the process is not universally applicable since only isocyanate prepolymers based on aliphatic polyisocyanates can be reacted with hydroxy ketimines with complete preservation of the ketimine structure.

According to German Offenlegungsschrift 2,338,256, high molecular weight, amine-terminated polyether urethane ureas are prepared by the reaction of prepolymers containing free isocyanate groups with amines in highly dilute solutions and then hardened with epoxide resins. The use of the solvents required for this process, in particular the aromatic solvents, is technically and physiologically undesirable. On the other hand, the viscosity of the solvent free reaction products is too high for practical use.

U.S. Pat. Nos. 4,291,146, 4,360,655 and 4,424,336 describe the use of relatively low molecular weight aminocrotonates as curing agents for epoxide resins. The use of the crotonates described in these references leads to cured epoxides which have poor flexibility for many purposes, i.e., less than about 30% elongation.

U.S. Pat. No. 5,021,537 describes a coating composition which comprises an epoxy resin, a polyacetoacetate, a curing agent for the epoxy resin and an optional solvent. Recently, novel amine compounds and processes for their production have been discovered. These compounds correspond to the formula:

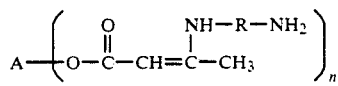

wherein A represents the polyfunctional radical left by the removal of the hydroxyl groups from a polyol of molecular weight of from 62 to 12,000, and preferably from about 800 to about 3500 and functionality n, R represents an arylene radical of from 6 to 21 carbon atoms, and n is an integer of from 2 to 6, preferably from 2 to 4. See U.S. application Ser. No. 523,769, filed on May 15, 1990. In addition, U.S. application Ser. Nos. 524,268, filed on May 15, 1990, and 562,293, filed on Aug. 3, 1990, relate to production techniques for similar compounds which can contain aliphatic as well as aromatic bound amine groups. Similar compounds and their methods of production can be found in U.S. Pat. Nos. 3,666,726 and 3,691,112 and in European Patent 363,000.

The present invention is directed to the discovery that the novel amine compounds noted are eminently suitable for use with epoxide group containing resins.

DESCRIPTION OF THE INVENTION

The present invention is directed to a curable composition comprising:

a) an epoxide compound with, on average, more than one epoxide group in the molecule, and b) a β-aminocrotonate of the general formula:

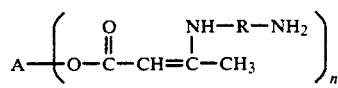

where

R represents a hydrocarbon radical,

A represents the polyfunctional radical left by removal of the hydroxyl groups from a polyol of molecular weight of from about 800 to about 6000 and functionality n, and n is an integer of from 2 to 6, with the ratio of component a) to component b) being such that at least one half moles of amine groups are present for each mole of epoxide group. The cured resins produced from this composition exhibit excellent physical properties and are particularly notable as far as their flexibility.

Useful aminocrotonates include those of the formula:

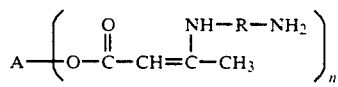

$$A\left(O-\underset{\underset{}{\overset{O}{\overset{\|}{C}}}}-CH=\underset{\underset{CH_3}{|}}{\overset{NH-R-NH_2}{\overset{|}{C}}}\right)_n$$

wherein A represents the polyfunctional radical left by the removal of the hydroxyl groups from a polyol of molecular weight of from 800 to 6,000 and preferably from about 800 to about 3500 and functionality n, R represents a hydrocarbon radical, and n is an integer of from 2 to 6, preferably from 2 to 4. R may be aromatic, aliphatic or cycloaliphatic and is preferably a hydrocarbon radical selected from the group consisting of an arylene radical of from 6 to 21 carbon atoms, a straight or branched chain alkylene radical of from 2 to 20 carbon atoms, a cycloalkylene radical of from 3 to 20 carbon atoms, a $C_7$ to $C_{20}$ alkarylepe radical, and a $C_7$ to $C_{20}$ aralkylene radical, with the proviso that 1) the amine groups must be separated by 2 or more than 3 carbon atoms if R is an alkylene or aralkylene radical and 2) the amine groups can not be in ortho positions to each other if R is an arylene or alkarylene radical. R is most preferably an aliphatic radical of from 5 to 12 carbon atom As used herein, the term "arylene" is intended to mean a divalent radical derived from an aromatic hydrocarbon (which can be monoaromatic, diaromltic or polyaromatic) by removal of a hydrogen atoms from each of two carbon atoms of the aromatic moiety. Specific examples include tolylene, phenylene, naphthylene, diphenylene, and the like. As used herein, the term is also intended to include diaromatic radicals such as methylenebis(phenyl), isopropylenebis(phenyl) and the like. The key is that both of the nitrogen atoms of the above formula be directly attached to an aromatic radical. As noted above, the amine groups can not be in ortho positions to each other.

As used herein, the term "alkylene" is intended to mean a divalent radical derived from an aliphatic hydrocarbon by removal of a hydrogen atom from each of two carbon atoms of the aliphatic moiety. Specific examples include ethylene, butylene, and the like. As noted above, the amine groups must be separated by 2 or more than 3 carbon atoms.

As used herein, the term "cycloalkylene" is intended to mean a divalent radical derived from a cycloaliphatic hydrocarbon by removal of a hydrogen atom from each of two carbon atoms of the cycloaliphatic moiety. Specific examples include cyclobutylene, cyclopentylene, cyclohexylene and the like.

As used herein, the term "alkarylene" is intended to mean a divalent radical derived from an aromatic hydrocarbon (which can be monoaromatic, diaromatic or polyaromatic) which is substituted with one or more alkyl groups by removal of a hydrogen atom from each of two carbon atoms of the aromatic moiety. As noted above, the amine groups can not be in ortho positions to each other.

As used herein, the term "aralkylene" is intended to mean a divalent radical derived from an aliphatic hydrocarbon which is substituted with one or more aryl groups by removal of a hydrogen atom from each of two carbon atoms of the aliphatic moiety. As noted above, the amine groups must be separated by 2 or more than 3 carbon atoms.

The aminocrotonates useful herein are prepared by reacting a polyfunctional acetoacetic acid ester with an organic compound which contains two primary amino groups. The reaction may be conducted in the presence of a solvent and an acidic catalyst selected from the group consisting of (i) boron trifluoride etherate and (ii) organic acids having pKa values of from 0.1 to 0.8. In the case of aromatic amines, a catalyst is essential. By this invention, it is possible to use a Wide variety of different aminocrotonates having a wide variety of different reactivities by selection of the primary amino compound used in the preparation thereof.

The polyfunctional acetoacetic acid esters useful herein are produced by techniques generally known in the art. For example, the acetoacetic acid esters may be produced according to the processes described in U.S. Pat. Nos. 3,666,726 and 3,691,112, and U.S. application Ser. Nos. 523,769 and 524,268, both filed on May 15, 1990, and U.S. Pat. No. 562,293, filed on Aug. 3, 1990, all of the disclosures of which are herein incorporated by reference. In general, the acetoacetic acid esters can be produced by reacting polyols with diketenes, or by transesterifying alkylacetoacetates with polyols. The transesterification technique is the presently preferred technique. In general, the transesterification reaction is conducted at temperatures ranging from 100° to 210° C. for periods of time ranging from 2 to 24 hours. If desired, transesterification catalysts, such as dibutyltin oxide and tetrabutyl titanate, can be used.

The polyols useful in producing the polyfunctional acetoacetic acid esters are of the type generally used in polyurethane chemistry. The polyols useful herein typically have molecular weights of from 800 to 6000, preferably from about 800 to about 3500 and have hydroxyl functionalities of from 2 to 6, preferably from 2 to 4. Examples of suitable compounds include the polyesters, polyethers, polythioethers, polyacetals, polybutadienes and polycarbonates containing 2 to 6 hydroxyl groups of the type known for the production of polyurethanes. The polyethers suitable for use in accordance with the invention are known and may be obtained, for example, by polymerizing epoxides such as ethylene oxide, propylene oxide, butylene oxide, tetrahydrofuran, styrene oxide or epichlorohydrin in the presence of $BF_3$ or by chemically adding these epoxides, preferably ethylene oxide and propylene oxide, in admixture or successively to components containing reactive hydrogen atoms such as water, alcohols or amines. Examples of alcohols and amines include low molecular weight diols, triols and tetrols, 4,4'-dihydroxy diphenyl propane, sorbitol, aniline, ammonia, ethanolamine and ethylene diamine.

Suitable examples of polyesters include the reaction products of polyhydric, preferably dihydric alcohols (optionally in the presence of trihydric alcohols), with polyvalent, preferably divalent, carboxylic acids. Instead of using the free carboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic, and/or heterocyclic and may be unsaturated or substituted, for example, by halogen atoms. The polycarboxylic acids and polyols used to prepare the polyesters are known and described for example in U.S. Pat. Nos. 4,098,731 and 3,726,952, herein incorporated by reference in their entirety. Suitable polythioethers, polyacetals, polycarbonates and other polyhydroxyl compounds are also disclosed in the above-identified U.S. patents. Finally, representatives of the many and varied polyols which may be used in accordance with the invention may be found for example in High Polymers, Volume XVI, "Polyurethanes, Chemistry and Technology," by Saunders-Frisch, Interscience Publishers, New York, London, Vol I, 1962, pages 32-42 and 44-54, and Volume II, 1964, pages 5-6 and 198-199; and in Kunststoff-Handbuch, Vol. VII, Vieweg-Hochtlen, Carl Hanser Verlag, Munich, 1966, pages 45-71.

Polyols useful herein also include materials which are typically used as chain extenders in polyurethane chemistry. Examples of such materials include ethylene glycol, 1,2- and 1,3-propane diol, 1,3- and 1,4- and 2,3-butane diol, 1,6-hexane diol, 1,10-decane diol, diethylene glycol, triethylene glycol, tetraethylene glycol, dipropylene glycol, tripropylene glycol, glycerol, trimethylol propane, and pentaerythritol.

The polyfunctional acetoacetic acid esters are preferably prepared by transesterifying any of the above noted polyols with lower alkyl acetoacetates. By "lower alkyl" is meant alkyl groups containing from one to five carbon atoms. Specific useful acetoacetates include methyl acetoacetate, ethyl acetoacetate, t-butyl acetoacetate, propyl acetoacetate and the like, with t-butyl acetoacetate being the presently preferred material. In preparing the acetoacetic acid esters herein, transesterification catalysts may be necessary. In preparing the polyfunctional acetoacetic acid esters, it is generally preferred that the reactants be used in amounts such that one OH group is present for each acetoacetate group. However, it is also possible to use excess amounts of either reactant. In fact, in some cases it is preferred to use an excess of the acetoacetate to ensure complete reaction.

The polyfunctional acetoacetic acid ester is then reacted with a primary diamine.

The solvents which can be used herein are of the same type described in U.S. Pat. Nos. 3,666,726, and 3,691,112. Preferred solvents are those that form azeotropes with water. Suitable solvents include methylene chloride, chloroform, chlorobenzene, dichlorobenzenes, toluene, xylenes, ethylacetate, propylacetate, butylacetate, diethylether, dibutylether, and the like. Toluene is the presently preferred solvent. The amount of solvent is generally selected so as to be sufficient for dissolving the starting materials. In general, the solvent is used in a quantity of from 20 to 500, and preferably from 50 to 200 parts by weight per 100 parts by weight of the polyfunctional acetoacetic acid ester.

The catalyst, if used, is selected from the group consisting of boron trifluoride etherate and organic acids having pKa values of from 0.1 to 0.8. It has been found that use of catalysts having pKa values outside the range noted leads to side reactions which lead to solid products. In addition, only the catalysts noted lead to commercially acceptable yields. Of the acids tested, only trifluoroacetic acid (pKa: 0.23) and p-toluene sulfonic acid (pKa: 0.7) were found useful in preparing amines from aromatic amine compounds. The amount of catalyst is generally selected so as to be sufficient to allow reasonable reaction times. In practice, the catalyst is added in amounts of from 0.05 to 2.0 mole %, and preferably from 0.3 to 1.0 mole %, based on the equivalents of acetoacetate present. This corresponds to from 0.01 to 0.2 % by weight, and preferably from 0.05 to 0.1 % by weight based on the weight of the polyfunctional acetoacetic acid ester.

Useful amines which are to be reacted with the polyfunctional acetoacetic acid esters are primary aliphatic, cycloaliphatic and aromatic diamines. Specific amines include diethyltoluene diamine and the various isomers and isomer mixtures thereof; toluene diamine and the various isomers and isomer mixtures thereof; methylenebis(phenyl amine) and the various isomers and isomer mixtures thereof; 1,5-naphthalene diamine; t-butyl toluene diamine, and the various isomers and isomer mixtures thereof; di-tibutyl toluene diamine, and the various isomers and isomer mixtures thereof; methylenebis(o-dichloroaniline) ("MOCA"); 2,4-diaminoalkybenzenes, and homologues and isomers thereof having alkyl radicals of from 8 to 15 carbon atoms as described in published European Patent Application 58,368; ethylene diamine; the various straight and branched chain isomers of diaminobutane, diaminopentane, diaminohexane, diaminoheptane, diaminooctane, diaminononane, and diaminodecane; the various isomers of diaminocyclobutane, diaminocyclopentane, diaminocyclohexane, diaminocycloheptane, diaminocyclooctane, diaminocyclononane, diamino-1-methylcyclohexane, methylenebis(cyclohexyl amine), diamino-1-methylcyclopentane, diaminodimethylcyclohexane; isophorone diamine; and the like. One presently preferred aliphatic diamine is 1,5-diamino-2-methylpentane.

The amount of amine is generally selected so that one mole of diamine is available for every acetoacetate equivalent. It is of course possible to react less than one mole diamine with one equivalent of acetoacetate. This might result in a lower conversion if the reaction is terminated before all acetozo acetate groups have reacted with amine groups, or in chain extension if all acetoacetate groups have reacted. On the other hand, in order to suppress chain extension and to obtain low viscosity products, it might be advantageous to use more than one mole diamine per equivalent of acetoacetate. The unreacted diamine can either be stripped off once the reaction is complete, or can remain in the product to serve as a chain extender, i.e., in a reaction with isocyanates.

The reaction is generally carried out at temperatures of from 40° to 200° C., preferably from 90° to 140° C., under excess pressure, reduced pressure, or, preferably, in the substantial absence of pressure. The process can be conducted continuously or discontinuously. In general, the acetoacetic acid ester, the amines, and the catalyst are dissolved in the solvent. The reaction mixture is refluxed while the water of reaction is collected. When no more water comes off, the reaction is considered complete. The reaction time, of course, depends on the nature and the amounts of starting materials. In general, reaction times are between 1 and 6 hours. When the reaction is complete, the catalyst and any unreacted amine (if desired) are distilled off. The distillate can generally be recycled.

Mixtures of the products according to the invention and epoxide resins are heat curable and cold curable. Suitable epoxide resins are known and are described, e.g., in U.S. Pat. Nos. 4,291,146, 4,360,655 and 4,424,336, the disclosures of which are herein incorporated by reference. These epoxides contain on average more than one epoxide group per molecule and may be glycidyl ethers of polyhydric alcohols such as butane diol, hexane diol, glycerol or hydrogenated diphenyl propane or of polyvalent phenols such as resorcinol, diphenylol propane or phenolaldehyde condensates.

Glycidyl ethers of polybasic carboxylic acids such as hexahydrophthalic acid or dimerized fatty acid may also be used.

It is particularly preferred to use liquid epoxide resins having molecular weights from 340 to 450 based on epichlorohydrin and diphenylol propane. The viscosity of the mixture may be lowered, if desired, by means of monofunctional epoxide compounds, whereby the processing properties are improved. Examples of such epoxide compounds include aliphatic and aromatic glycidyl ethers such as butylglycidyl ether and phenylglycidyl ether or glycidyl esters such as glycidyl acrylate or epoxides such as styrene oxide and 1,2-epoxydodecane.

The products of the process according to the invention may be mixed with other amine hardeners of the type known from epoxide resin chemistry before their use according to the invention. Examples of these hardeners include the usual amine hardeners used in this field, e.g. polyamino amides optionally containing imidazoline groups.

Curing of the mixtures according to the invention is effected by warming the mixtures to temperatures of between 100° and 250° C., and preferably 100° to 200° C. for periods of time of from about 0.2 to about 24 hours, whereupon the mixtures are converted to high molecular weight polymers without the emission of volatile reaction products.

For the preparation of mixtures ready for use, the usual auxiliary agents and additives such as fillers, pigments, reaction accelerators and viscosity regulators may be incorporated in the combinations of epoxide resins and hardeners according to the invention. Examples of such additives include reaction accelerators such as salicylic acid, bis-(dimethyl-aminomethyl)-phenol and tris-(dimethylaminomethyl)-phenol; fillers such as sand, powdered rock, silica, powdered asbestos, kaolin, talc, metal powder, tar, tar pitch, asphalt, cork scrap, and polyamides; plasticizers such as phthalic acid esters and other viscosity regulators such as, for example, benzyl alcohol. Epoxide resin hardener combinations in which the products of the process of the invention are used as all or part of the hardeners are suitable for the production of coatings, adhesives, sealing compounds and molded parts in all fields of application where good adherence, chemical resistance and high impact strength and shock resistance are required in combination with improved flexibility and elasticity.

The invention is further illustrated but is not intended to be limited by the following examples in which all parts and percentages are by weight unless otherwise specified.

EXAMPLES

Preparation of acetoacetylated polyols

The apparatus consisted of (i) a vacuum jacketed distillation column with metal packing, (ii) a variable reflux ratio distilling head with a round bottom flask attached to receive alkanol and excess alkyl acetoacetate, (iii) a five liter three neck flask, and (iv) a thermoregulator and a heating mantle. The following polyols were used:

POLYOL A: a polyoxypropylene glycol having a molecular weight of about 1000.

POLYOL B: a polyoxypropylene glycol having a molecular weight of about 2000.

POLYOL C: a polyoxypropylene triol from glycerine and propylene oxide having a molecular weight of about 3000.

The five liter flask was charged with the polyol, and nitrogen was bubbled through the flask, and the temperature was raised to 130° C. t-butyl acetoacetate ("tBAA" in Table below) was charged into an addition funnel and added to the flask dropwise. At the completion, the temperature was raised to 160° C. t-butanol ("tB" in Table below) was collected in the receiving flask. Once the t-butanol stopped coming off, vacuum was slowly applied to remove residual t-butanol and unreacted t-butyl acetoacetate. The amount of t-butanol collected was noted and the product characterized by IR. The disappearance of the hydroxyl peak around 3500-3400 cm$^{-1}$ indicated the completion of the reaction. The average time of the acetoacetylation was two hours. The acetoacetylated products were produced using the materials and amounts of materials noted in the following Table 1:

TABLE 1

| Acetoacetylated Product | Polyol Used | pbw polyol | pbw tBAA | pbw tB collected |
|---|---|---|---|---|
| 1 | A | 3000 | 950 | 444 |
| 2 | B | 3000 | 475 | 222 |
| 3 | C | 3000 | 475 | 222 |

Preparation of the aminocrotonates

The following amines were used:
DYTEK A: 2-methyl-1,5-diaminopentane
IPDA: isophoronediamine
PACM: 4,4-diaminodicyclohexylmethane
TCD: bis(aminomethyl)tricyclodecane
AEP: N-aminoethylpiperazine A five liter flask was charged with 3000 parts by weight of the acetoacetylated polyol ("AAP") and equimolar amounts of diamine ("DA"). The flask was fitted with a condenser with a dry ice cooled receiving flask. The reaction mixture was stirred and nitrogen was bubbled through the mixture. The temperature was raised to about 105° C. and gradually raised to 110° C. under vacuum (5mm Hg) The temperature was maintained at 110° C. for an additional two hours. At this point, most of the expected water of reaction had distilled off. To complete the reaction, the temperature was raised to 120° C. and kept at that temperature for another 30 minutes. The materials and amounts of materials used as well as the viscosities of the final product were as indicated in the following Table 2:

TABLE 2

| Aminocrotonate | AAP | DA | pbw | viscosity @ 25° C. |
|---|---|---|---|---|
| 1 | 1 | DYTEK A | 594 | 2,890 |
| 2 | 1 | IPDA | 870 | 6,190 |
| 3 | 1 | PACM | 1076 | 14,440 |
| 4 | 2 | DYTEK A | 320 | 2,100 |
| 5 | 2 | IPDA | 470 | 3,900 |
| 6 | 2 | PACM | 580 | 6,470 |
| 7 | 2 | TCD | 536 | 6,780 |
| 8 | 2 | AEP | 356 | 1,640 |
| 9 | 3 | DYTEK A | 320 | 7,700 |
| 10 | 3 | AEP | 186 | 2,230 |

Application Examples 190 parts by weight of Epon 828 (a bisphenol A/diglycidyl ether epoxide resin available from Shell) were mixed With the amount of aminocrotonate ("ACT")

noted in Table 3 until the reaction mixture was homogeneous. The clear resin was then poured into an aluminum mold (15.2 cm×15.2 cm×1.8 cm) and cured at 100° C. for 24 hours. The aminocrotonates used and the amounts thereof, as well as the physical properties (tensile strength according to ASTM D-412; elongation according to ASTM D-638; and tear strength according to ASTM 0-612) were as noted in the following Table 3:

TABLE 3

| ACT | ACT pbw. | Shore Hardness A | Shore Hardness D | Tensile strength psi | Elongation. % | Tear Strength, pli |
|---|---|---|---|---|---|---|
| 1 | 341 | 81 | — | 734.2 | 66.1 | 1141.0 |
| 2 | 368 | — | 45 | 1740 | 80.4 | 133.9 |
| 3 | 388 | — | 55 | 1867 | 62.8 | 169.9 |
| 4 | 591 | 50 | — | 187 | 55.3 | 550.1 |
| 5 | 618 | 61 | 22 | 326.3 | 71.8 | 26.13 |
| 6 | 638 | 76 | 20 | 452.8 | 65.2 | 29.89 |
| 7 | 630 | 75 | 21 | 397.6 | 58.6 | 24.80 |
| 8 | 598 | 32 | — | 185.5 | 80.4 | 14.68 |
| 9 | 591 | 66 | — | 265.4 | 38.6 | 752.0 |
| 10 | 1098 | 12 | — | 115.9 | 28.1 | 18.25 |

Comparison Examples

In these comparison examples, the following amine hardeners were used:

D-2000: Jeffamine D-2000, a commercially available polyether polyamine available from Texaco, having an amine equivalent of 1000.

V-140: Versamid 140, a reactive polyamide resin having an amine equivalent of 134, and being commercially available from Henkel.

190 parts by weight of Epon 828 were mixed with the amount of amine ("AMINE") noted in Table 4 until the reaction mixture was homogeneous. The clear resin was then poured into an aluminum mold (15.2 cm×15.2 cm×1.8 cm) and cured at 100° C. for 24 hours. The amine used and the amounts thereof, as well as the physical properties were as noted in the following Table 4:

TABLE 4

| AMINE | pbw | Shore Hardness A | Shore Hardness D | Tensile psi | Elongation. % | Tear Strength. pli |
|---|---|---|---|---|---|---|
| D-2000 | 500 | 54 | — | 105.7 | 18.3 | 572 |
| V-140 | 67 | — | 84 | 8000.0 | 10.0 | — |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A heat curable composition comprising:
   a) an epoxide compound with, on average, more than one epoxide group in the molecule, and
   b) a β-aminocrotonate of the general formula:

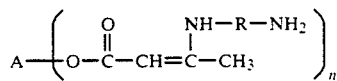

where
R represents a hydrocarbon radical,
A represents the polyfunctional radical left by removal of the hydroxyl groups from a polyol of molecular weight of from about 800 to about 6000 and functionality n, and
n is an integer of from 2 to 6,
with the ratio of component a) to component b) being such that at least one half moles of amine groups are present for each mole of epoxide group.

2. The composition of claim 1, wherein A represents the polyfunctional radical left by removal of the hydroxyl groups from a polyol of molecular weights of from about 800 to about 3,500.

3. The composition of claim 2, wherein n is an integer of from 2 to 4.

4. The composition of claim 3, wherein R is an aliphatic group having from 5 to 12 carbon atoms.

* * * * *